United States Patent [19]

Price

[11] Patent Number: 4,541,596
[45] Date of Patent: Sep. 17, 1985

[54] PORTABLE INTRAVENOUS POLE FOR USE IN AN EMERGENCY

[76] Inventor: Ronald K. Price, 2004 NW. 48th St., Oklahoma City, Okla. 73118

[21] Appl. No.: 592,858

[22] Filed: Mar. 23, 1984

Related U.S. Application Data

[63] Continuation-in-part of Ser. No. 417,094, Sep. 13, 1982, abandoned.

[51] Int. Cl.$^4$ .............................................. A47B 97/00
[52] U.S. Cl. ..................................... 248/125; 248/159
[58] Field of Search .................................. 604/141, 93; 128/DIG. 12; 248/125, 188.6, 188.7, 161, 159, 121, 165, 166

[56] References Cited

U.S. PATENT DOCUMENTS

| | | | |
|---|---|---|---|
| 3,026,079 | 3/1962 | Stack | 248/125 |
| 3,298,648 | 1/1967 | Stepanski | 288/125 X |
| 3,804,355 | 4/1974 | Uroshevich | 248/125 |
| 4,090,514 | 5/1978 | Hinck et al. | 128/DIG. 12 X |

Primary Examiner—Stephen C. Pellegrino

[57] ABSTRACT

The present invention is a portable intravenous pole for use in combination with a surface on which an emergency victim is lying and the weight of the emergency victim's body to support an intravenous delivery system including a container in which an intravenous solution is disposed. The portable intravenous pole includes a plurality of segments each of which is an elongated member having a first end and a second end. Each segment has at its first end a hook with a locking slot disposed adjacent thereto and at its second end a pivot bar. The pivot bar is rotatively coupled to the hook of another segment and is slidably inserted into the locking slot in order to fixedly, but detachably, couple together the segments. The portable intravenous pole also includes a base which is disposed perpendicular and fixedly coupled to one of the segments at its first end adjacent to the bottom of the portable intravenous pole. The base has a pair of hooks each of which has a locking slot disposed adjacent thereto. The portable intravenous pole further includes a pair of legs. Each leg is a flat elongated member having a pivot bar at one end. The pivot bar of each leg is rotatively coupled to one of the hooks of the base and is slidably inserted into one of the locking slots in order to fixedly, but detachably, couple the leg to the base. The pair of legs supports the base and the mechanically coupled segments in a substantially vertical position so that the intravenous delivery system is disposed above the body of the emergency victim.

4 Claims, 11 Drawing Figures

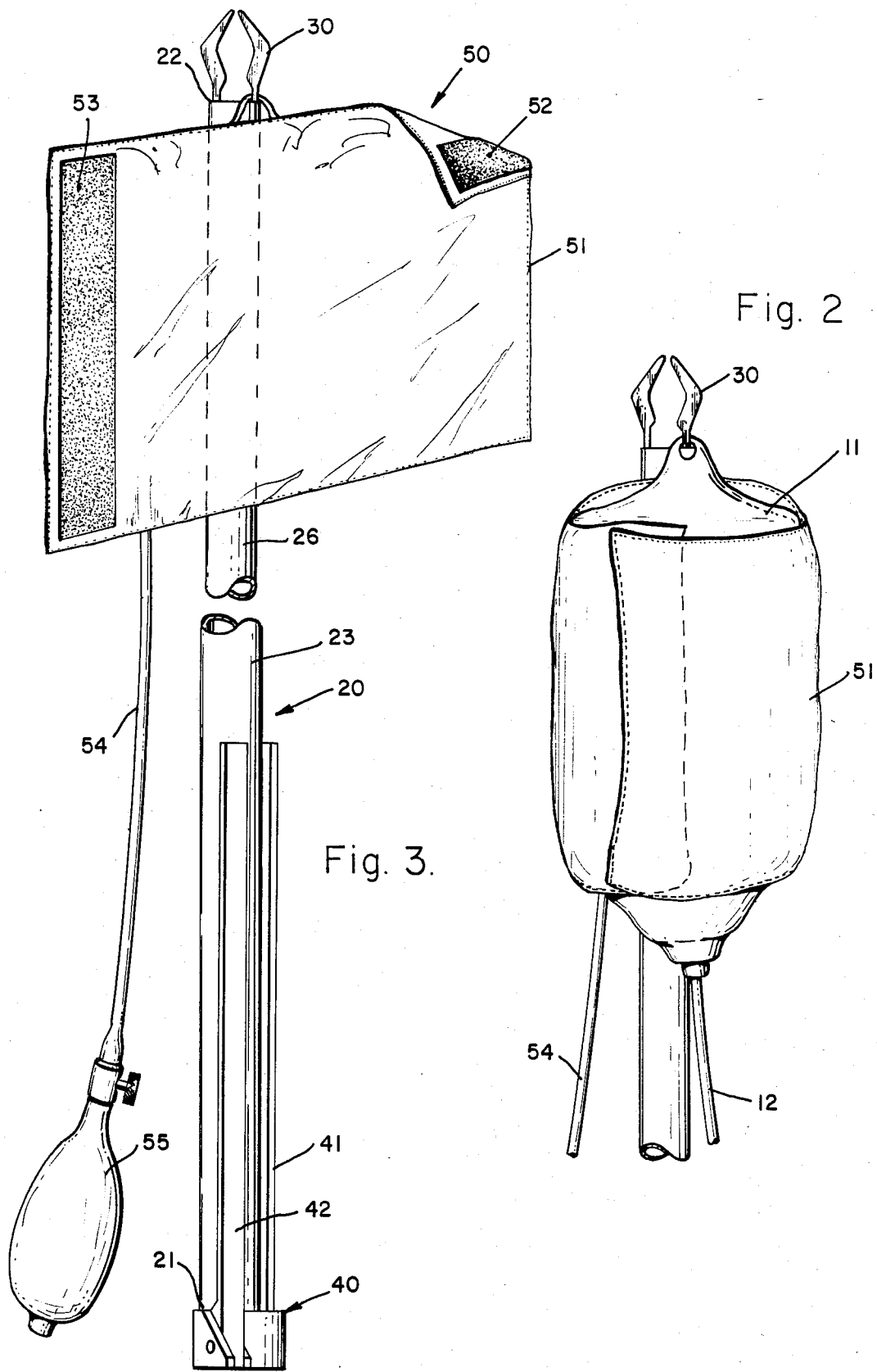

U.S. Patent  Sep. 17, 1985  Sheet 3 of 3  4,541,596
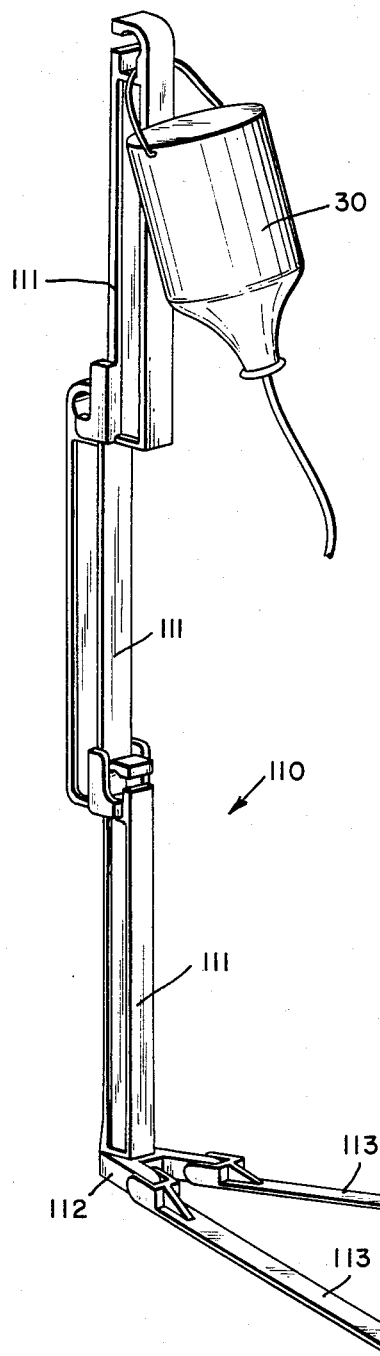
Fig. 6.
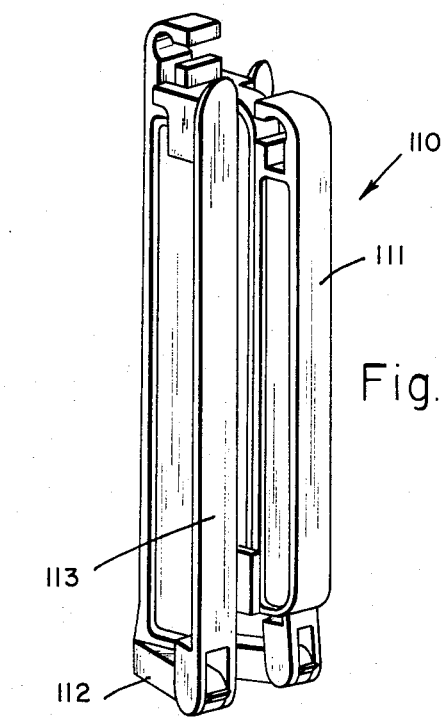
Fig. 7.
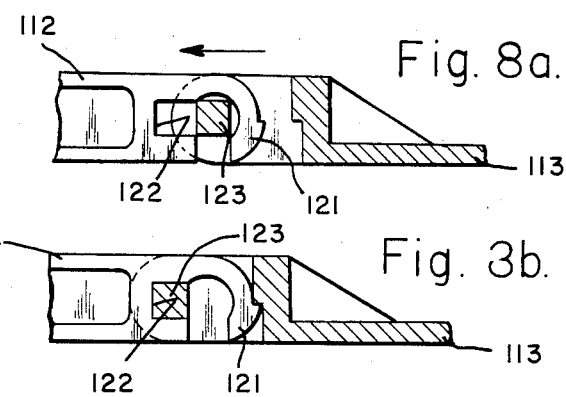
Fig. 8a.
Fig. 8b.
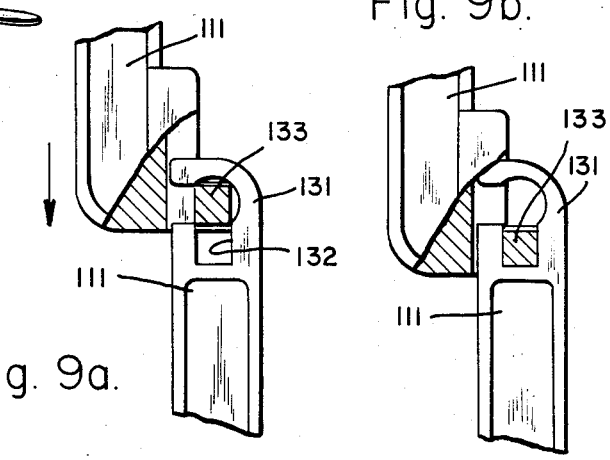
Fig. 9a.
Fig. 9b.

PORTABLE INTRAVENOUS POLE FOR USE IN AN EMERGENCY

This application is a continuation-in-part of the application having a Ser. No. 417,094, filed on Sept. 13, 1982 now abandoned.

BACKGROUND OF THE INVENTION

1. Field of the Invention

The present invention relates to an intravenous use in an emergency and more particularly to a portable intravenous pole which may be used in combination with a stretcher or gurney and the weight of the emergency victim's body to support an intravenous solution delivery system during transport of the emergency victim to the ambulance.

2. Description of the Prior Art

U.S. Pat. No. 4,355,639, entitled Apparatus the Parenteral Administration of Liquids at a Constant Flow Rate, issued to Francisco Di Salvo on Oct. 26, 1982, teaches an intravenous pole.

U.S. Pat. No. 4,332,378, entitled Ambulatory Patient Support Stand, issued to John W. Pryor on June 1, 1982, teaches a support stand which includes a wheeled support for an ambulatory patient. The support stand utlizes wide span legs together with its low center of gravity and a low horizontal push point. The patient grips the support stand through a toroidal ring grip. A user may suspend an intravenous bottle from a pole supported above the toroidal ring grip.

U.S. Pat. No. 4,090,514, entitled Pressure Infusion Device, issued to Howard Hemut Hinck on May 23, 1978, teaches a pressure infusion device which includes a bladder as part of the cuff in which a fluid filled plastic bag is encassed wherein the bladder surrounds at least eighty percent of the plastic bag, and upon fluid being pumped into the bladder, the fluid in the plastic bag is infused under pressure to a patient.

U.S. Pat. No. 3,804,355, entitled Collapsible Supporting Stand, issued to Miroslav Uroshevich on Apr. 16, 1974, teaches a collapsible supporting stand which has a tripodal base with legs which are pivotally mounted at the bottom of a base shaft. The supporting arm is pivotally mounted to a vertical shaft which is slidably mounted in the base shaft. The collapsible supporting stand also has an adjusting mechanism for the supporting arm and the vertical shaft.

U.S. Pat. No. 3,298,648, entitled Baby Bottle Holder, issued to Russell J. Sepanski on Apr. 8, 1966, teaches a baby bottle holder which has a base which a user disposes underneath the back of a baby and a bottle mount which is mechanically coupled to the base and which receives a baby bottle so that a user may suspend a baby bottle above a baby so that the baby may drink from the baby bottle.

U.S. Pat. No. 1,082,808, entitled Bottle Holder, issued to Norman Hubbard on Dec. 30, 1913, teaches a baby bottle holder which is similar to the baby bottle holder of U.S. Pat. No. 3,298,648.

U.S. Pat. No. 4,169,550, entitled Emergency Medical Kit, issued to Paul K. Williams on Oct. 2, 1979, teaches an emergency medical kit which has a plurality of pockets and straps which are designed to hold medical equipment. The pocket are selectively closable to prevent the loss of the equipment retained therein. In an unfolded position, the medical kit can be spread upon a flat surface, or suspended from a hanger, such that the medical equipment is readily accessible to medical personnel. In a folded position, the medical kit is attachable to a person's back so medical equipment and supplies can be transported to areas inaccessible via motor vehicles. There is a life support liter which is a lightweight self-contained system for emergency cardio-pulmonary resuscitation and which includes a backboard, contoured to automatically hyperextend neck for maintenance of open airway, an oxygen supply system, and an intravenous pole, coupled to a life support liter so that an emergency victim can receive both an intravenous solution and oxygen while being transported.

U.S. Pat. No. 4,286,588, entitled Medical Support Board, issued to Paul D. Lovegrove on Sept. 1, 1981, teaches a medical support board to inhibit movement of a patient's limb. The medical support board has an adherent strip applied to its reverse side. The adherent strip is removably adherable to materials underlying the support board such as carpets, blankets or the clothing of the patient. The adherent strip adherring to an underlying material inhibits movement of the patient's limb relative to the body. Straps are provided to secure the limb to the support board and are fastened by means of adherent strips.

U.S. Pat. No. 4,292,969, entitled Fluid Regulating Device with Torsional Control, issued to Donald A. Raible, Stuart M. Potichs and Rita Stauffer on Oct. 6, 1981, teaches an improved fluid regulating device which is used in a parenteral administration system having tubing. The device provides torsional flexture of the tubing by relative rotation between first and second body members to regulate fluid flow. U.S. pat. No. 4,292,969 teaches an intravenous pole which is typical of the prior art.

U.S. Pat. No. 4,190,280, entitled Wheeled Patient Support, issued to Sephen C. Donohoe on Feb. 26, 1980, teaches a wheeled patient support which includes a platform secured to the unit laterally beyond the periphery of the unit and substantially below the patient supporting surface with a rolling surface mounted to and beneath the platform so that an attendant can stand on the platform and treat the patient while the patient is being wheeled to the area of treatment.

U.S. Pat. No. 4,097,941, entitled Emergency Cot with a Spring-Biased Retractable Wheel Carriage, issued to Jerome L. Merkel, teaches an emergency cot for transporting a patient. None of the emergency cots and stretchers has an intravenous pole coupled to it. The lack of an intravenous pole necessitates a third person carrying the intravenous solution delivery system above an emergency victim while he is being transported on either an emergency cot or a stretcher by two other attendants. In a large scale emergency where there may be a number of victims this use of a third person is not only inefficient, but also unsafe to the emergency victim.

SUMMARY OF THE INVENTION

In view of the foregoing factors and conditions which are characteristic of the prior art it is the primary object of the present invention to provide an intravenous pole for use in an emergency which may be used in combination with either a stretcher or a gurney and the weight of the emergency victim's body to support an intravenous solution delivery system during transport of the emergency victim to the ambulance.

It is another object of the present invention to provide an intravenous pole for use in delivering an intravenous solution to an emergency victim while transporting him which eliminates the need for a third person to carry the intravenous bag.

It is still another object of the present invention to provide an intravenous pole for use in delivering an intravenous solution to an emergency victim while he laying on ground awaiting to be transported from an accident or diaster site.

In accordance with the present invention an embodiment of the present a portable intravenous pole for use in combination with a surface on which an emergency victim is lying and the weight of the emergency victim's body to support an intravenous delivery system including a container in which an intravenous solution is disposed is described. The portable intravenous pole includes a plurality of segments each of which is an elongated member having a first end and a second end. Each segment has at its first end a hook with a locking slot disposed adjacent thereto and at its second end a pivot bar. The pivot bar is rotatively coupled to the hook of another segment and is slidably inserted into the locking slot in order to fixedly, but detachably, couple together the segments. The portable intravenous pole also includes a base which is disposed perpendicular and fixedly coupled to one of the segments at its first end adjacent to the bottom of the portable intravenous pole. The base has a pair of hooks each of which has a locking slot disposed adjacent thereto. The portable intravenous pole further includes a pair of legs. Each leg is a flat elongated member having a pivot bar at one end. The pivot bar of each leg is rotatively coupled to one of the hooks of the base and is slidably inserted into one of the locking slots in order to fixedly, but detachably, couple the leg to the base. The pair of legs supports the base and the mechanically coupled segments in a substantially vertical position so that the intravenous delivery system is disposed above the body of the emergency victim.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 2 is a perspective drawing of an intravenous container and a top portion of the portable intravenous pole of FIG. 1.

FIG. 3 is a perspective drawing of a bottom portion and a top portion of the portable intravenous pole of FIG. 1.

FIG. 6 is a perspective drawing of a second portable intravenous pole which has been constructed in accordance with the principles of the present invention and which is shown in use.

FIG. 7 is a perspective drawing of the second portable intravenous pole of FIG. 6 which is folded so that it can be conveniently store or transported.

FIG. 8a is a partial side elevational view in cross-section of a base and leg of the second portable intravenous pole of FIG. 6 showing them rotatively coupled to each other.

FIG. 8b is a partial side elevational view in cross-section of a base and leg of the second portable intravenous pole of FIG. 6 showing them fixedly, but detachably, coupled to each other.

FIG. 9a is a partial side elevational view in cross-section of two segments of the second portable intravenous pole of FIG. 6 showing them rotatively coupled to each other.

FIG. 9b is a partial side elevational view in cross-section of two segments of the second portable intravenous pole of FIG. 6 showing them fixedly, but detachably, coupled to each other.

DESCRIPTION OF THE PREFERRED EMBODIMENT

Figure 1:
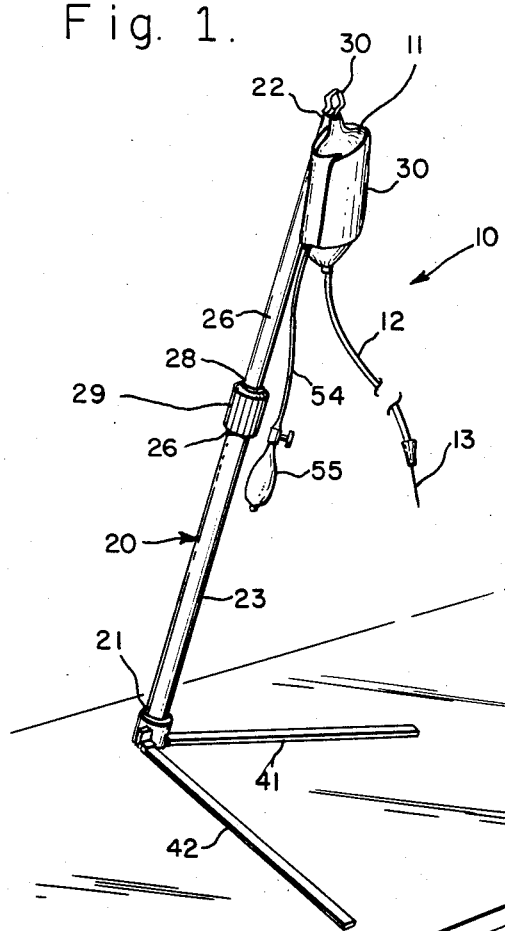
FIG. 1 is a perspective drawing of a first portable intravenous pole which has been constructed in accordance with the principles of the present invention.

In order to best understand the present invention it is necessary to refer to the following description of its preferred embodiment in conjunction with the accompanying drawing. Referring to FIG. 1 a portable pole a portable intravenous pole 10 for use in combination with a surface on which an emergency victim is lying and the weight of the emergency victim's body to support an intravenous solution delivery system.

Referring to FIG. 1 in conjunction with FIG. 2 the intravenous delivery system includes a container 11 in which an intravenous solution is disposed, tubing 12 which is fluidly coupled to the container 11, and a fluid input device 13 which is fluidly coupled to the tubing 12 for insertion into a vein of the emergency victim. The portable intravenous pole 10 includes a telescopic, elongated member 20 which has a bottom end 21 and a top end 22 and which includes a first elongated tubular member 23 having a first end and a second end 25 with the first end corresponding to the bottom end 21 and a second elongated tubular member 26 having a first end and a second end 28 with the first end corresponding to the top end 22. The second end 28 of the second elongated tubular member 26 is telescopically coupled into the second end 25 of the first elongated tubular member. A clamping device 29 clamps and holds the first and second elongated tubular members 23 and 26 in a predetermined telescopic relationship. The portable intravenous pole 10 also includes a claw 30 for mounting the container 11 to the top end 22.

Figure 4:
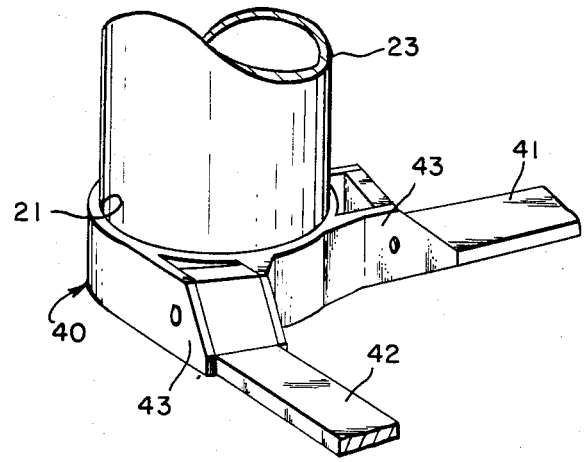
FIG. 4 is a perspective drawing of a mount of the portable intravenous pole of FIG. 1.

Referring to FIG. 3 in conjunction with FIG. 1 and FIG. 4 the portable intravenous pole 10 further includes a support member 40 which supports the elongated member 20 in a substantially vertical position whereby the container 11 is disposed above the body of the emergency victim.

Figure 5:
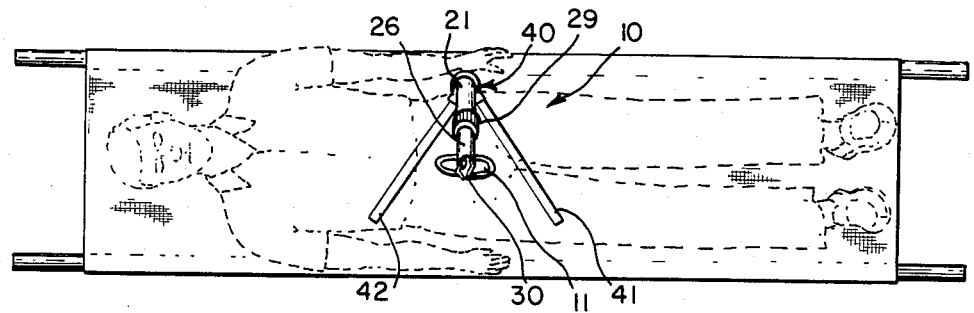
FIG. 5 is a top plan view the intravenous container and the portable intravenous pole of FIG. 1.

Referring to FIG. 5 in conjunction with FIG. 1 and FIG. 4 the support member 40 is mechanically coupled to the bottom end 21 so that the support member 40 may be placed between the surface on which the emergency victim is lying and the body of the emergency victim. The support member 40 includes first and second elongated, rectangular bars 41 and 42 which are relatively flat and a mount 43 which pivotally couples the the first and second elongated, rectangular bars 41 and 42 to the bottom end 21 wherein each of the first and second elongated, rectangular bars 41 and 42 rotates within an angular range of 0° to 90° with respect to the elongated member 40 and wherein the pivoting end of the second elongated, rectangular bar 42 is disposed radially apart from the pivoting end of the first elongated, rectangular bar 41 an angle in the range of 45° to 120°. A locking mechanism 44 locks the pivoting ends of the first and second elongated, rectangular bars 41 and 42 in place.

Referring again to FIG. 1 in conjunction with FIG. 1 and FIG. 3 the portable intravenous pole 10 has a container compression system 50 which includes a rectangular air bag 51 which is formed from a flexible material and which is mechanically coupled to the claw 30. The container compression system 50 also includes a male velcro stip 52 and a female velcro strip 53 for mechanically coupling the opposing ends of the rectangular air bag 51 so that the rectangular air bag 51 wraps around the container 11. The container compression system 50 further includes a piece of tubing 54 and an air pump 55 for pressurizing the rectangular air bag 51 whereby the intravenous solution is forced out of the container 11. The container compression system 50 is very useful in the event of a patient who is in shock and needs a quick infusion of the intavenous solution.

Referring to FIG. 6 in conjunction with FIG. 7 a second portable intravenous pole 110 for use in combination with a surface on which an emergency victim is lying and the weight of the emergency victim's body to support an intravenous delivery system including a container 30 in which an intravenous solution is disposed. The second portable intravenous pole 110 includes a plurality of segments 111 each of which is an elongated member having a first end and a second end. The second portable intravenous pole 110 also includes a base 112 which is disposed perpendicular and fixedly coupled to one of the segments at its first end adjacent to the bottom of the second portable intravenous pole 110.

Referring to FIG. 8a and FIG. 8b the base 112 has a pair of hooks 121 each of which has a locking slot 122 disposed adjacent thereto. The second portable intravenous pole 110 further includes a pair of legs 113. Each leg 113 is a flat elongated member having a pivot bar 123 at one end. The pivot bar 123 of each leg 113 is rotatively coupled to one of the hooks 131 of the base 112 and is slidably inserted into one of the locking slots 122 in order to fixedly, but detachably, couple the leg 113 to the base 113. The pair of legs 113 supports the base 112 and the mechanically coupled segments 111 in a substantially vertical position so that the intravenous delivery system is disposed above the body of the emergency victim.

Referring to FIG. 9a and FIG. 9b each segment 111 has at its first end a hook 131 with a locking slot 132 disposed adjacent thereto and at its second end a pivot bar 133. The pivot bar 133 is rotatively coupled to the hook 131 of another segment 111 and is slidably inserted into the locking slot 133 in order to fixedly, but detachably, couple together the segments 111.

From the foregoing it can be seen that a portable intravenous pole has been described. It should be noted that the sketches are not drawn to scale and that distances of and between the figures are not to be considered significant.

Accordingly it is intended that the foregoing disclosure and showing made in the drawing shall be considered only as an illustration of the principles of the present invention.

What is claimed is:

1. A portable intravenous pole for use in combination with a surface on which an emergency victim is lying and the weight of the mergency victim's body to support a intravenous solution delivery system including a container in which an intravenous solution is disposed, tubing fluidly coupled to the container, and a fluid input device fluidly coupled to the tubing for insertion into a vein of the emergency victim, said portable intravenous pole comprising:
   a. a plurality of segments each of which is an elongated member having a first end and a second end wherein said first end of one of said plurality of segments may be mschanically coupled to said second end of another of said plurality of segments;
   b. mounting means for mounting the container to said first end of one of said plurality of segments;
   c. a base which is disposed perpendicular and fixedly coupled to one of said plurality of segments at its said first end adjacent to the bottom of said portable intravenous pole wherein said base has pair of hooks each of which has a locking slot disposed adjacent thereto and said supporting means has a pair of legs each of which is a flat elongated member having a pivot bar at one end and which are mechanically coupled to said base whereby said pivot bar of each of said pair of legs is rotatively coupled to one of said hooks and is slidably inserted into one of said locking slots thereby fixedly, but detachably, coupling each of said pair of legs to said base; and
   d. supporting means for supporting said base and said plurality of segments in a substantially vertical position whereby the container is disposed above the body of the emergency victim, said supporting means being mechanically coupled to said base so that said supporting means may be placed between the surface on which the emergency victim is lying and the body of the emregency victim.

2. A portable intravenous pole according to claim 1 wherein each of said plurality of segments has at its said first end a hook which has a locking slot disposed adjacent thereto and has at its said second end a pivot bar whereby said pivot bar is rotatively coupled to said hook and is slidably inserted into said locking slot thereby fixedly, but detachably, coupled together said plurality of segments.

3. A portable intravenous pole for use in combination with a surface on which an emergency victim is lying and the weight of the emergency victim's body to support a intravenous solution delivery system including a container in which an intravenous solution is disposed, tubing fluidly coupled to the container, and a fluid input device fluidly coupled to the tubing for insertion into a vein of the emergency victim, said portable intravenous pole comprising:
   a. a plurality of segments each of which is an elongated member having a first end and a second end wherein said first end of one of said plurality of segments may be mechanically coupled to said second end of another of said plurality of segments wherein each of said plurality of segments has at its said first end a hook which has a locking slot disposed adjacent thereto and has at its said second end a pivot bar whereby said pivot bar is rotatively coupled to said hook and is slidably inserted into said locking slot thereby fixedly, but detachably, coupling together said plurality of segments;

b. mounting means for mounting the container to said first end of one of said plurality of segements;

c. a base which is dispoed perpendicular and fixedly coupled to one of said plurality of segments at its said first end adjacent to the bottom of said portable intraveous pole; and d. supporting means for supporting said base and said plurality of segments in a substantially vertical position whereby the container is disposed above the body of the emergency victim, said supporting means being mechanically coupled to said base so that said supporting means may be placed between the surface on which the emergency victim is lying and the body of the emergency victim.

4. A portable intravenous pole according to claim 3 wherein said base has a pair of hooks each of which has a locking slot disposed adjacent thereto and said supporting means has a pair of legs each of which is a flat elongated member having a pivot bar at one end and which are mechanically coupled to said base whereby said pivot bar of each of said pair of legs is rotatively coupled to one of said hooks and is slidably inserted into one of said locking slots thereby fixedly, but detachably, coupling each of said pair of legs to said base.

* * * * *